United States Patent [19]

Kubota et al.

[11] 4,350,150

[45] Sep. 21, 1982

[54] STRUCTURE OF A LIGHT-RECEIVING END PORTION OF AN ENDOSCOPE LIGHT GUIDE

[75] Inventors: Tetsumaru Kubota; Kenji Koyata, both of Hachioji, Japan

[73] Assignee: Olympus Optical Co., Ltd., Tokyo, Japan

[21] Appl. No.: 187,545

[22] Filed: Sep. 16, 1980

[30] Foreign Application Priority Data

Sep. 25, 1979 [JP] Japan ................................ 54-122936

[51] Int. Cl.$^3$ ................................................ A61B 1/06
[52] U.S. Cl. ........................................................ 128/6
[58] Field of Search ...................... 128/4, 5, 6, 7, 8, 9; 350/96.23, 96.24, 96.25, 96.26; 354/62, 63

[56] References Cited

U.S. PATENT DOCUMENTS

| | | | |
|---|---|---|---|
| 2,699,770 | 1/1955 | Fourestier et al. | 128/6 |
| 3,261,350 | 7/1966 | Wallace | 128/6 |
| 4,157,216 | 6/1979 | Plummer | 128/6 X |
| 4,215,678 | 8/1980 | Heine et al. | 128/6 |

FOREIGN PATENT DOCUMENTS

| | | | |
|---|---|---|---|
| 1311018 | 3/1973 | United Kingdom | 128/6 |
| 2041559 | 9/1980 | United Kingdom | 128/6 |

*Primary Examiner*—Gene Mancene
*Assistant Examiner*—Robert P. Swiatek

[57] ABSTRACT

A light-receiving end structure of an endoscope light guide comprises the illumination light-receiving end plane formed on an illumination light-receiving end portion of the light guide, an adhesive agent applied to the illumination light-receiving end portion to bond together optical fibers constituting the end portion, a transparent heat-resistant disc member mounted on the illumination light-receiving end plane, and a metal support surrounding the light-receiving end portion and the disc member in a liquid-tight state. The heat generated by light beams irradiated on the light-receiving end plane is conducted through the disc member to the support and then released into the open air. Therefore, the light-receiving end portion is not exposed to a high temperature. Accordingly, the light-receiving end structure is prominently increased in effective life.

16 Claims, 8 Drawing Figures

STRUCTURE OF A LIGHT-RECEIVING END PORTION OF AN ENDOSCOPE LIGHT GUIDE

This invention relates to a structure of a light-receiving end portion of an endoscope light guide.

Illumination of a coeliac cavity of, for example, a human body by an endoscope is generally carried out by introducing illumination light beams issued from a light source set outside of the endoscope into the coeliac cavity through a light guide formed of an optical fiber bundle extending through the endoscope from its control section (or operation section).

The optical fibers of the light-receiving end portion of the light guide extending from the control section of the endoscope are tightly bundled together by an adhesive in a liquid-tight state. The optical fiber bundle is fixed to a connector. When the connector is fitted into a receptacle of a light source device, light beams emitted from the light source are converged by a converging lens at the light-receiving end plane of the light guide projecting from the control section of the endoscope.

However, the conventional structure of a light-receiving end portion of an endoscope light guide which is not provided with means for dissipating heat resulting from the convergence of illumination light beams issued from a light source at the light-receiving end plane of the light guide has the drawback that great heat is built up at the light-receiving end plane; where the endoscope is repeatedly used, an adhesive applied to the optical fiber bundle is subject to deterioration and denaturation and will lose a liquid-tight property; and consequently moisture invades from the light-receiving end plane of the light guide into spaces between the respective optical fibers, thereby prominently reducing the light-transmitting property of the light guide.

An object of the invention is to provide a structure of a light-receiving end portion of an endoscope light guide which reliably renders the light-receiving end portion liquid-tight.

Another object of this invention is to provide a structure of a light-receiving end portion of an endoscope light guide, wherein a light-receiving end plane of the light guide is provided with means for dissipating heat resulting from the convergence of illumination light beams sent forth from a light source at the light-receiving end plane of the light guide, thereby preventing the deterioration and denaturation of an adhesive agent applied to the optical fibers of the light-receiving end portion, and enabling the light guide to retain its original light-transmitting property.

A structure embodying this invention comprises an illumation light-receiving end portion of a light guide formed of a bundle of optical fibers and having an illumination light-receiving end plane, an adhesive applied to the light-receiving portion to fix the respective optical fibers together, a transparent heat-resistant disc member concentrically mounted on the light-receiving end plane, and a metal support sealingly surrounding the disc member.

The disc member is formed of a heat-resistant type of glass material. It is also possible to let the interior or surface of the disc member be traversed by highly heat-conductive fine metal wires.

Provision of the disc member on the light-receiving end plane ensures sealing of the illumination light-receiving end portion from the atmosphere.

Moreover, heat absorbing means is provided on one of the two end faces of the disc member or in the disc member.

The heat of illumination light beams emitted from a source to the light-receiving end portion of the light guide is mostly absorbed by the heat-absorbing means. The absorbed heat is transmitted to a tubular fixing member to be finally dissipated into the open air. Therefore, the following advantages are ensured that heat is not noticeably generated in the light-receiving end portion of the light guide; the adhesive agent is not exposed to high temperature, but is saved from thermal deterioration and denaturation; and moisture is not carried into spaces between optical fiber, thereby enabling the light guide to retain its original light-transmitting property.

That end of the fixing member by which the disc member is supported may be provided with an annular caulked portion which holds the outer edge of the disc member. This arrangement ensures the liquid-tight condition of the light-receiving end portion of the light guide.

Further, the fixing member may be provided with a head member, a body portion surrounding the light receiving end portion of the light guide and a head portion receiving the disc member and threadedly coupling the head portion and the body portion together. This arrangement allows for the easy replacement of a cylindrical member without obstructing the liquid-tight state of the light-receiving end portion of the light guide.

This invention can be fully understood from the following detailed description with reference to the accompanying drawings in which:

FIG. 1 schematically illustrates an endoscope equipped with a structure embodying this invention;

Figure 1:
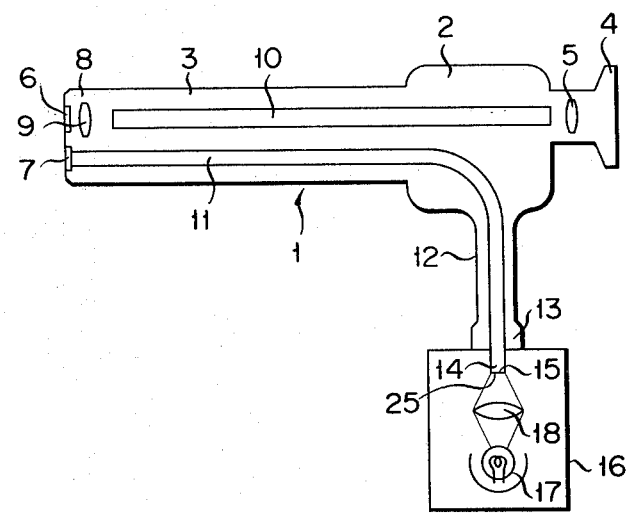

FIG. 1 schematically illustrates an endoscope equipped with a structure embodying this invention. An endoscope 1 is not different from the conventional type, but is formed of a control section (or operation section) 2 and flexible sheath 3 extending from the control section 2. An eyepiece section 4 containing an ocular lens 5 is mounted on the rear end of the control section 2. An observation window 6 and illumination window 7 are formed side by side in the front end of the distal end portion 8 of the sheath 3. An objective 9 facing the observation window 6 is provided in the distal end portion 8. An image guide 10 formed of an image-transmitting optical fiber bundle extends through the endoscope 1. One end of the image guide 10 is optically connected to the ocular lens 5 and the other end thereof faces the objective 9.

One end of a light guide 11 formed of an illumination light-transmitting optical fiber bundle is optically connected to the illumination window 7. The light guide 11 passes through the sheath 3 and projects from the control section 2 at an intermediate part of the light guide 11. The projecting portion of the light guide 11 is inserted into a protective tube 12 projecting likewise from the control section 2. An end structure 14 of the light guide 11 which has a plane 15 of the other end at the light guide 11 is fixed to the connector 13 mounted on the remote side of the protective tube 12 from the control section 2.

When the connector 13 is fitted into a connector receptacle (not shown) of a light source device 16, light beams emitted from a lamp 17 of high luminosity such as a xenon lamp housed in the light source device 16 are converged on the end plane 15 by a converging lens 18 set in the light source device 16. The plane 15 at the other end of the light guide 11 is hereinafter referred to as "a light-receiving end plane 15," and the end structure 14 of the light guide 11 is hereinafter referred to as "a light-receiving end structure 14." The connector 13 and its receptacle used in this invention are of the known structure, description thereof being omitted.

Figure 2:
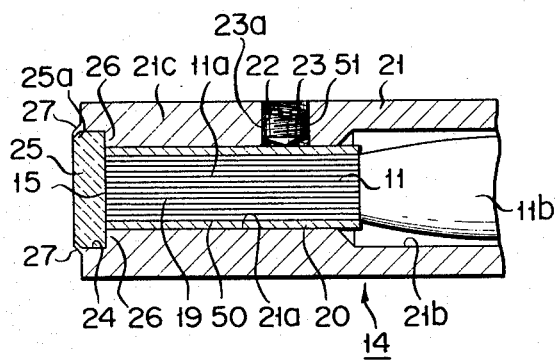
FIG. 2 is a longitudinal sectional view of a structure according to one embodiment of this invention.

FIG. 2 shows a light-receiving end structure 14 according to one embodiment of this invention. The optical fiber part 19 of the light-receiving end portion 11a of the light guide 11, that is, the light-receiving end part of the bundle of the optical fibers are tightly bonded together by a heat-resistant adhesive agent 50 such as glass resin. The light-receiving end portion 11a is securely set in a cylindrical fixing member 20 made of highly heat-conductive metal such as copper, brass or stainless steel by an adhesive agent in a liquid-tight state. A hollow cylindrical support 21 is made of highly heat-conductive metal such as brass, aluminium or copper. This support 21 is provided with a bore 21a whose inner diameter is substantially the same as the outer diameter of the fixing member 20 and into which the fixing member 20 is inserted, and another bore 21b which receives the portion 11b of the light guide 11 contiguous to the light-receiving end portion 11a. Internal screw threads 22 are formed in the lateral wall 21c of the support 21. The external screw threads 23a of a set screw 23 are engaged with the internal screw threads 22, thereby causing the light-receiving end portion 11a of the light guide 11 to be fixed to the support 21. If, in this case, a sealing agent 51 such as silicone rubber which solidifies after application is coated on the external threads of the set screw 23 and thereafter the external threads 23a are fitted into the internal threads 22, a liquid-tight state is ensured between the internal threads 22 and the external threads 23a. An annular hole 24 having a larger diameter than the bore 21a and concentric therewith is formed in that end portion of the support 21 which is adjacent to the light-receiving end plane 15. A transparent heat-resistant disc member 25 is fitted into the annular hole 24. The outer edge of the backside of the disc member 25 is made to abut against a shoulder 26 formed between the bore 21a and annular hole 24. The outer edge 25a of the front side of the disc member 25 is held in the hollow cylindrical support 21 by means of an annular caulked or holding portion 27 formed on the front side of the support 21. The arrangement ensures a light-tight state between the outside and the light-receiving end plane 15 of the light guide 11. The annular caulked portion 27 is fabricated by the steps of providing an annular protuberance or ridge on the inner edge of the front end of the support 21, inserting the disc member 25 into the annular hole 24, caulking the annular protuberance toward the center of the disc member 25 by a caulking tool for contact with the outer edge 25a of the disc member 25.

The disc member 25 well serves the purpose if it is made of a transparent heat-resistant material. It is particularly preferred that the disc member 25 be prepared from a hightly heat-resistant material such as quartz glass or a hightly heat-resistant glass such as quartz or boron glass. Where, however, a great deal of heat is not expected to arise at the light-receiving end plane 15 of the light guide 11, the disc member 25 may be formed by an only slightly heat-resistant material such as white plate glass. The disc member 25 is chosen to have a thickness accounting for about 20% of the diameter of the light-receiving end plane 15.

In operation, where the connector 13 is fitted into the receptacle of the light source device 16 and the lamp 17 is lit, light beams issued from the lamp 17 are converged at the light-receiving end plane 15 of the light guide 11 through the light-converging lens 18. While the light beams pass through the disc member 25, most (for example, 50%) of the total heat generated by the light beams is absorbed by the disc member 25. The absorbed heat is dissipated into the open air through the thermally conductive support 21. As a result, transmission of heat to the light-receiving end portion 11a of the light guide 11 is suppressed, thereby preventing the temperature of the interior of the end portion 11a from being increased to such a high level as leads to the deterioration and denaturation of the adhesive agent 50 applied to the spaces defined between the respective optical fibers. Therefore, the light-receiving end portion 11a is not damaged by heat, nor is the liquid-tight state of the light-receiving end of the light guide 11 destroyed, thereby prominently prolonging the effective life of the light-receiving end structure 14.

The other edge 25a of the disc member 25 may be fixed to the front side of the support 21 by a heat-conductive bonding agent such as solder, instead of the annular caulked member 27. This arrangement enables heat to be effectively dissipated through the heat-conductive bonding agent, thereby preventing the temperature of the interior of the light-receiving end portion 11a from being excessively increased.

Figure 3:
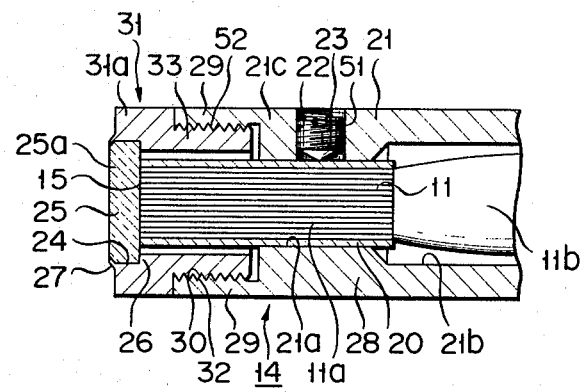
FIGS. 3 to 6 are longitudinal sectional views of a structure according to other embodiments of this invention, respectively.

Description is now given with reference to FIG. 3 of a light-receiving end structure 14 according to another embodiment of this invention. Internal screw threads 30 are formed in the inner wall of the distal end portion 29 of a support 21. The rear end portion of the support 21 is fixed to the connector 13 of FIG. 1. The support 21 comprises a support body 28 into which the light-receiving end portion 11a of a light guide 11 and a fixing member 20 are inserted, and a head member 31. The member 32 comprises a head portion 31a and the body portion 33. The disc member 25 is fitted into the annular hole 24 formed in the front end portion of the head portion 31a. On the outer lateral wall of the body portion 33 are provided external screw threads 32 engageable with the internal screw threads 30 of the distal end portion of the support 21. The other parts of the light-receiving end structure of FIG. 3 are the same as those of the preceding embodiment shown in FIG. 2.

Figure 4:
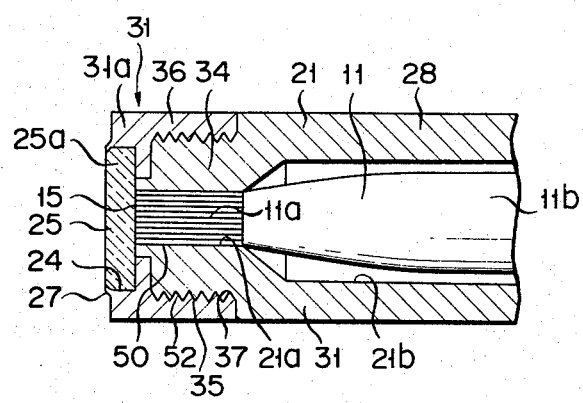

With a light-receiving end structure 14 according to still another embodiment of the invention shown in FIG. 4, the support 21 comprises a support body 28 having a head member 34 whose front end portion is provided with external screw threads 35 and a head member 31 having a head portion 31a and a skirt portion 36. Inner wall of the skirt portion 31a is provided with internal screw threads 37 engageable with the external screw threads 35 of the head member 34. With the embodiment of FIG. 4, the light-receiving end portion 11a of the light guide 11 is inserted into a bore 21a formed in the support body 28. The optical fibers of the light-receiving end portion 11a are bonded together by an adhesive agent 50 to be fixed to the support body 28 in a liquid tight state. In other words, the embodiment of FIG. 4 dispenses with the application of the fixing member 20 and a set screw 23 used in the embodiments of FIGS. 2 and 3, thereby simplifying the light-receiving end structure 14 and reducing the cost of manufacturing an endoscope as a whole.

With the embodiments of FIGS. 3 and 4, the head member 31 is detachably fitted to the front end portion of the support body 28, allowing for the easy replacement of the disc member 25 which is subject to heat damage. The head member 31 and support body 28 are threadedly engaged with each other so as to be rendered liquid-tight. If, in this case, both head member 31 and support body 28 are threadedly engaged with each other after applying the same kind of sealing agent as coated on the external screw threads of the fixing screw 23 of FIGS. 2 and 3, a liquid-tight state between both members is more ensured.

Figure 5:
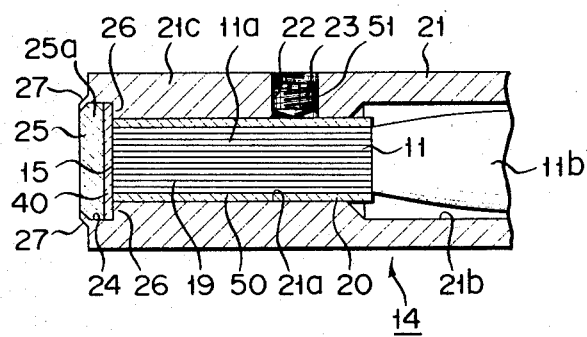

With the embodiment of FIG. 5, a heat absorbing filter 40 made of, for example, heat absorbing glass is disposed between a disc member 25 and the light-receiving end portion 11a of a light guide 11. The other construction is the same as that of the embodiment of FIG. 2. Heat from the light emitted into the filter 40 through the disc member 25 is absorbed by the filter 40, transmitted to a hollow cylindrical support 21 through a fixing member 20 and dissipated to the atmosphere. Thus, little heat is conducted to the light-receiving end portion 11a, preventing the heat damage of the portion 11a.

Figure 6:
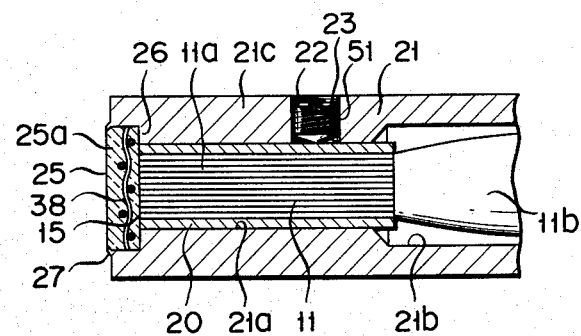
Figure 7:
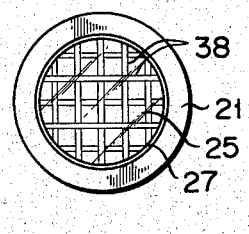
FIG. 7 is a front view of the structure of FIG. 6.
Figure 8:
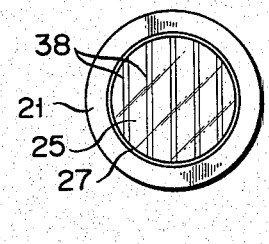
FIG. 8 is a front view of a structure according to a still further embodiment of this invention.

With a light-receiving end structure 14 according to a further embodiment of this invention shown in FIGS. 6 and 7, fine wires 38 of highly heat-conductive metal such as gold, silver or copper are embedded in the mesh form in the disc member 25 used in the embodiment of FIG. 2. This arrangement enables heat generated in the disc member 25 to be quickly dissipated into the open air through the fine metal wires 38. Therefore, temperature in the disc member 25 and consequently the light-receiving end portion 11a of the light guide 11 is more effectively prevented from being increased. The fine metal wires 38 need not be arranged in the mesh form, but may assume a striped pattern as illustrated in FIG. 8. In either case, it is preferred that a total area occupied by the fine metal wires 38 be about 10% of the area of the front face 25a of the disc member 25 in order to allow for the smooth introduction of light beams into the light guide 11. It is also possible to mount the fine metal wires 38 on the front face 25a of the disc member 25. The above-mentioned fine metal wires 38 are also applicable to the embodiments of FIGS. 3 to 5.

With the embodiments of FIGS. 2 to 7, the light-receiving end plane 15 of the light guide 11 abuts against the rear face of the disc member 25. However, the light-receiving end plane 15 may be set apart from the disc member 25. Then, heat is conducted from an air gap between the light-receiving end plane 15 and disc member 25 to the thermally conductive support 21. Therefore, the light-receiving end portion 11a of the light guide 11 is prevented from being highly heated. Moreover, the light-receiving end plane 15 is saved from damage resulting from impingement of the end plane 15 on the rear face of the disc member 25.

With the embodiments of FIGS. 2, 3, 5 and 6, heat of the light-receiving end portion 11a of the light guide 11 is transmitted to the support 21 through the fixing member 20. With the embodiment of FIG. 4, heat of the light-receiving end portion 11a is directly conducted to the support 21. In either case, the heat of the light-receiving end portion 11a is effectively dissipated.

What we claim is:

1. A structure of a light-receiving end portion of an endoscope light guide including a bundle of optical fibers comprising:
   an end part of the bundle of the optical fibers having an end plane for receiving light;
   an adhesive applied to the end part for fixing the optical fibers together;
   a support made of a metal of good heat conductivity, and provided with a bore into which said end part of the bundle of the optical fibers is inserted and also with an annular hole open to said bore and the outside; and
   a transparent heat-resistant disc member fitted into said annular hole in a liquid tight state.

2. The structure according to claim 1, wherein heat absorbing means is provided at the disc member.

3. The structure according to claim 2, wherein said heat absorbing means is fine wires of highly heat-conductive metal traversing the disc member.

4. The structure according to claim 3, wherein the fine metal wires are arranged in a mesh form.

5. The structure according to claim 3, wherein said fine metal wires are arranged in the striped pattern.

6. The structure according to claim 2, wherein said heat absorbing means is disposed in the disc member.

7. The structure according to any one of claims 2 to 5, wherein said heat absorbing means is a heat absorbing filter disposed between the disc member and the end plane of the optical fibers.

8. The structure according to claim 1 or claim 2, wherein said disc member is made of heat-resistant glass.

9. The structure according to claim 8, wherein the heat-resistant glass member is prepared from one selected from the group consisting of quartz and boron glass.

10. The structure according to claim 1, wherein the support comprises a support body which is provided with the bore, and a head member which is provided with the annular hole; the screw threaded engagement means is provided between the distal end portion of the support body and the rear end portion of the head member.

11. The structure according to claim 10, wherein said screw threaded engagement means is provided with a sealing agent.

12. The structure according to claim 1, wherein a tubular fixing member made of highly heat conductive metal is provided between said bore and said end part of the optical fiber; and a set screw is threadedly inserted across the support to securely hold the fixing member.

13. The structure according to claim 12, wherein a sealing agent is applied between the set screw and support.

14. The structure according to claim 1, wherein the support is provided with an annular holding portion for holding the disc member.

15. The structure according to claim 14, wherein said annular holding portion is an annular caulked portion.

16. The structure according to claim 14, wherein said annular holding portion is a soldered element.

* * * * *